United States Patent
Finley et al.

(10) Patent No.: US 8,644,953 B1
(45) Date of Patent: Feb. 4, 2014

(54) LEAD WITH BRAIDED REINFORCEMENT

(75) Inventors: James Finley, Minneapolis, MN (US); John Swoyer, Blaine, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/572,081

(22) Filed: Aug. 10, 2012

(51) Int. Cl.
*A61N 1/00* (2006.01)

(52) U.S. Cl.
USPC .......................................... 607/116; 607/122

(58) Field of Classification Search
USPC .......................................... 607/116–119, 122
See application file for complete search history.

(56) References Cited

U.S. PATENT DOCUMENTS

| | | | |
|---|---|---|---|
| 3,902,501 A | 9/1975 | Citron et al. | |
| 3,939,843 A | 2/1976 | Smyth | |
| 4,033,357 A | 7/1977 | Helland et al. | |
| 4,236,529 A | 12/1980 | Little | |
| 4,269,198 A | 5/1981 | Stokes | |
| 4,301,815 A | 11/1981 | Doring | |
| 4,402,328 A | 9/1983 | Doring | |
| 4,409,994 A | 10/1983 | Doring | |
| 4,414,986 A | 11/1983 | Dickhudt et al. | |
| 4,590,949 A | 5/1986 | Pohndorf | |
| 4,658,535 A | 4/1987 | Anderson | |
| 4,883,070 A | 11/1989 | Hanson | |
| 5,231,996 A * | 8/1993 | Bardy et al. | 607/126 |
| 6,213,995 B1 * | 4/2001 | Steen et al. | 604/527 |
| 6,701,191 B2 * | 3/2004 | Schell | 607/122 |
| 6,978,185 B2 * | 12/2005 | Osypka | 607/122 |
| 6,999,819 B2 | 2/2006 | Swoyer et al. | |
| 7,330,764 B2 | 2/2008 | Swoyer et al. | |
| 7,761,170 B2 * | 7/2010 | Kaplan et al. | 607/116 |
| 7,912,555 B2 | 3/2011 | Swoyer et al. | |
| 8,000,805 B2 | 8/2011 | Swoyer et al. | |
| 8,036,756 B2 | 10/2011 | Swoyer et al. | |
| 8,160,719 B2 * | 4/2012 | Swoyer et al. | 607/116 |
| 2002/0177888 A1 | 11/2002 | Williams et al. | |
| 2008/0183263 A1 | 7/2008 | Alexander | |
| 2009/0210043 A1 | 8/2009 | Reddy | |
| 2009/0281594 A1 | 11/2009 | King et al. | |
| 2010/0137928 A1 | 6/2010 | Duncan et al. | |
| 2011/0054581 A1 | 3/2011 | Desai et al. | |
| 2011/0054584 A1 | 3/2011 | Alexander et al. | |
| 2011/0160830 A1 | 6/2011 | Morris et al. | |
| 2011/0218603 A1 | 9/2011 | Victorine et al. | |
| 2012/0035616 A1 * | 2/2012 | Olsen et al. | 606/129 |
| 2012/0232625 A1 * | 9/2012 | Sage et al. | 607/116 |

* cited by examiner

*Primary Examiner* — Christopher D Koharski
*Assistant Examiner* — Catherine Voorhees
(74) *Attorney, Agent, or Firm* — Michael P. Horvath

(57) ABSTRACT

A therapy delivery element configured for at least partial insertion in a living body. A braided structure surrounds the conductor assembly. A distal end of the braided structure is attached to an electrode assembly and a free floating proximal end is located near a connector assembly. An outer tubing surrounds the braided structure. The outer tubing includes a proximal end attached to the connector assembly and a distal end attached to the braided structure near the electrode assembly. A proximal tension force applied to the connector assembly acts substantially on the outer tubing and the conductor assembly and a proximal tension force applied to the free floating proximal end acts substantially on the braided structure.

22 Claims, 13 Drawing Sheets

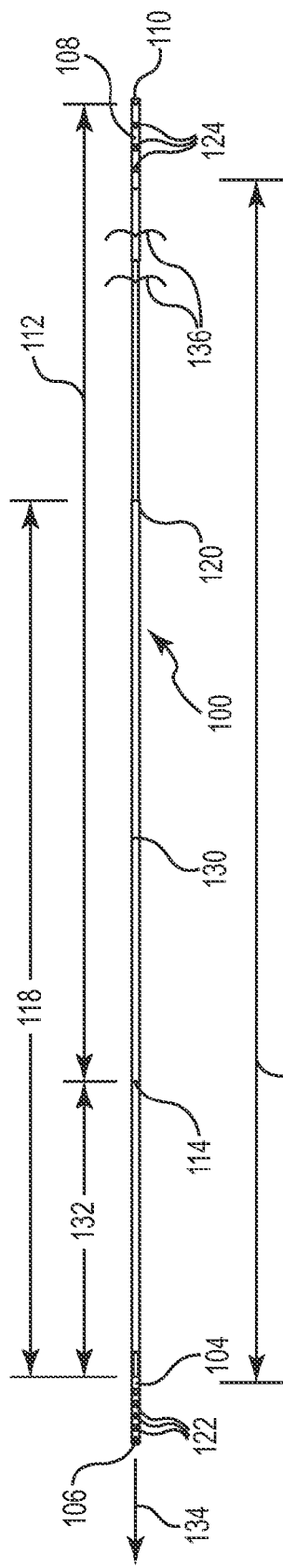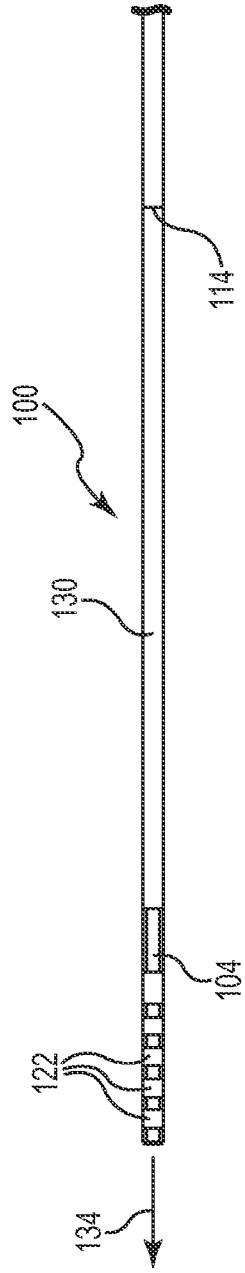

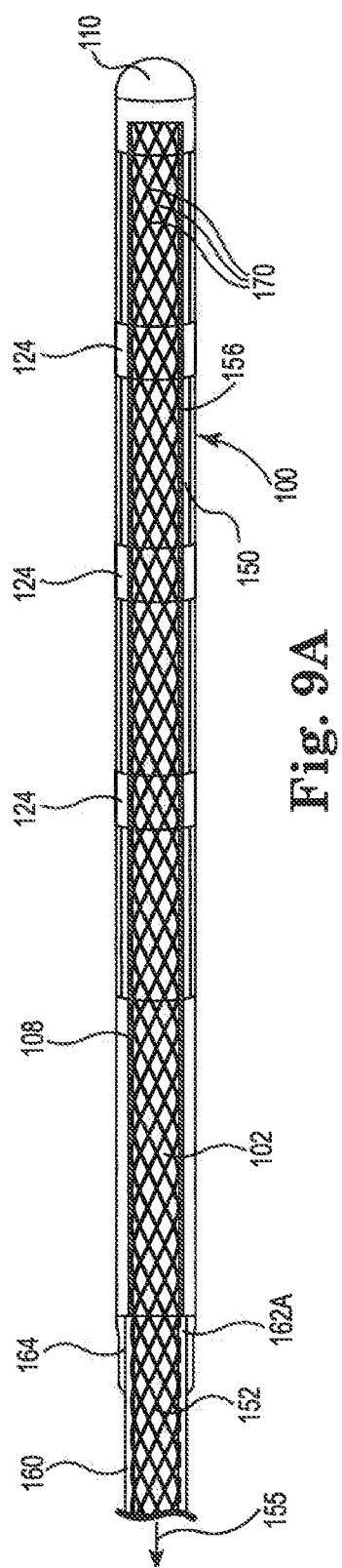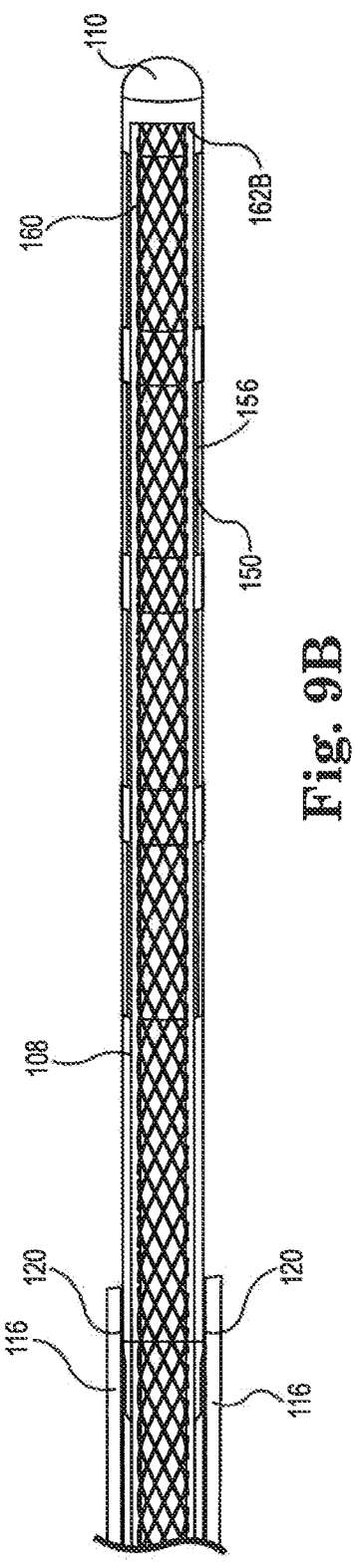

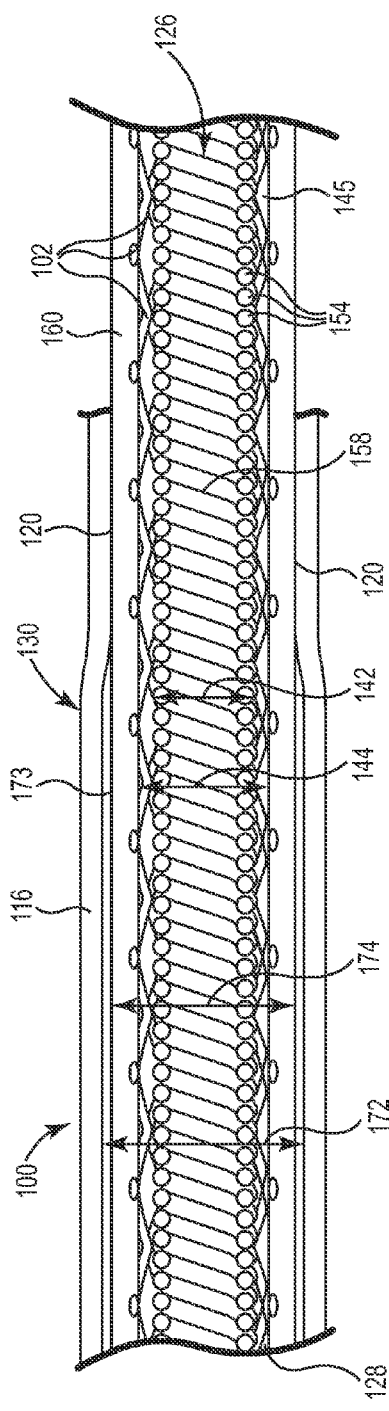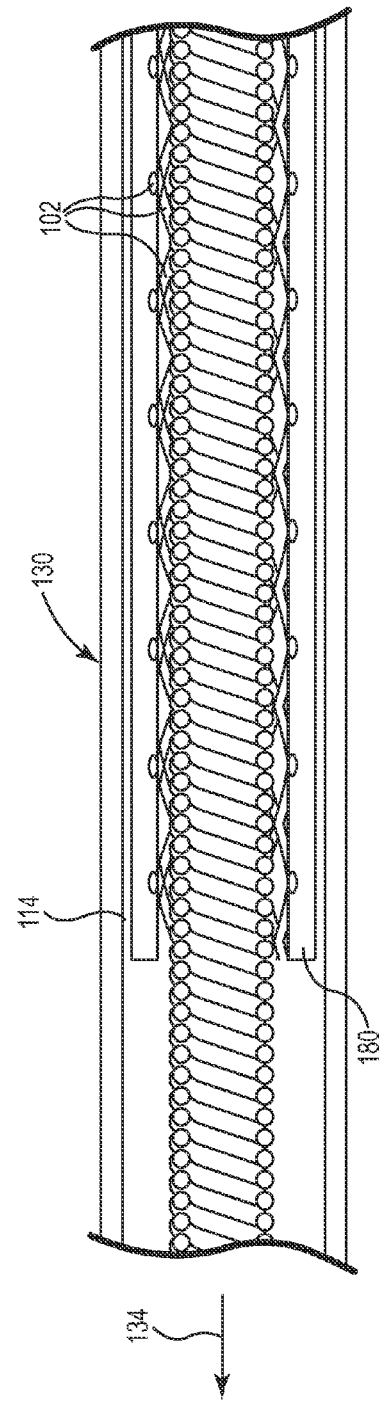
Fig. 10
Fig. 11

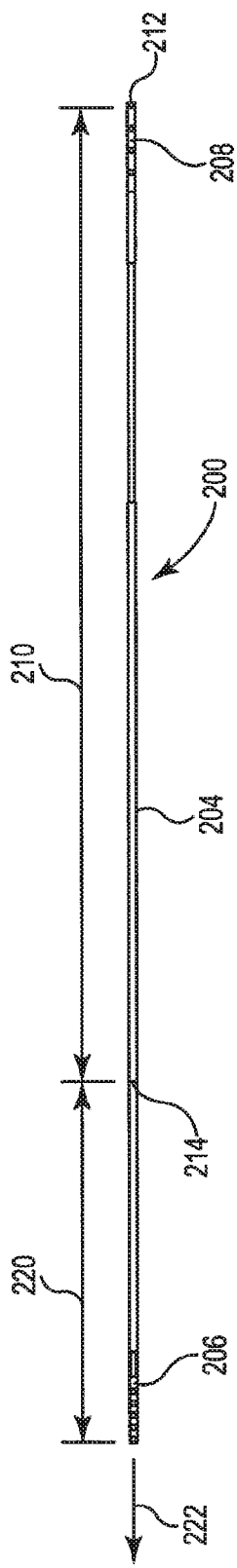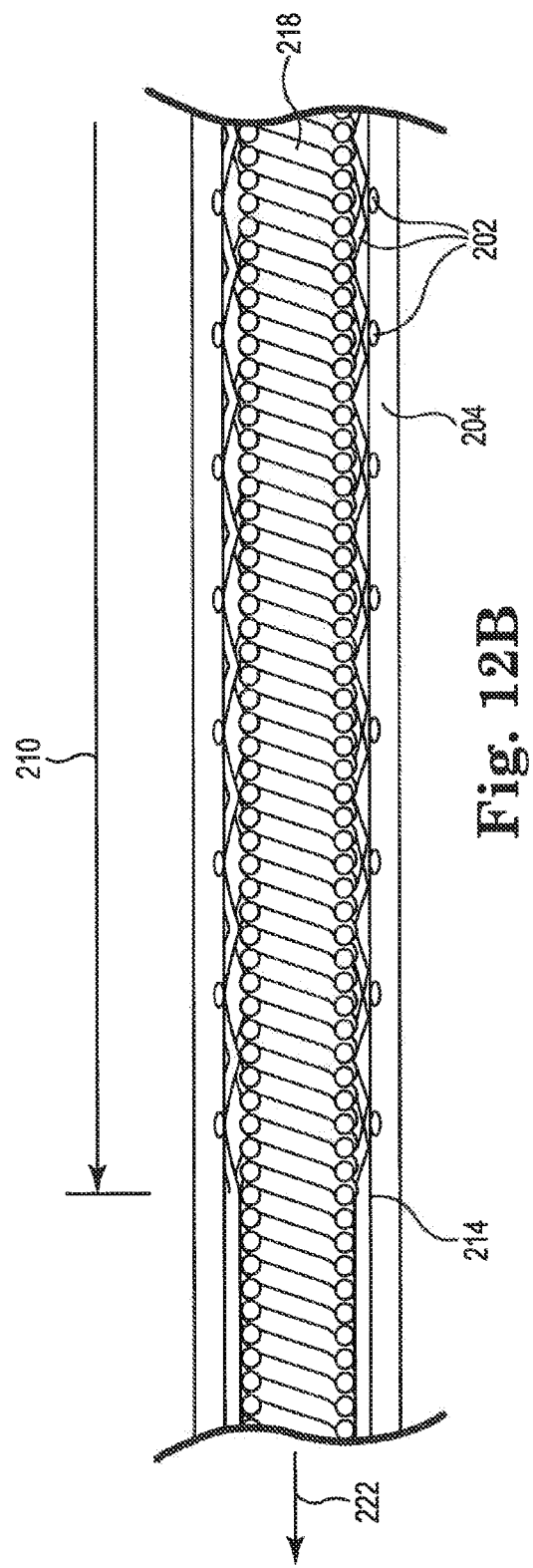
Fig. 12A
Fig. 12B

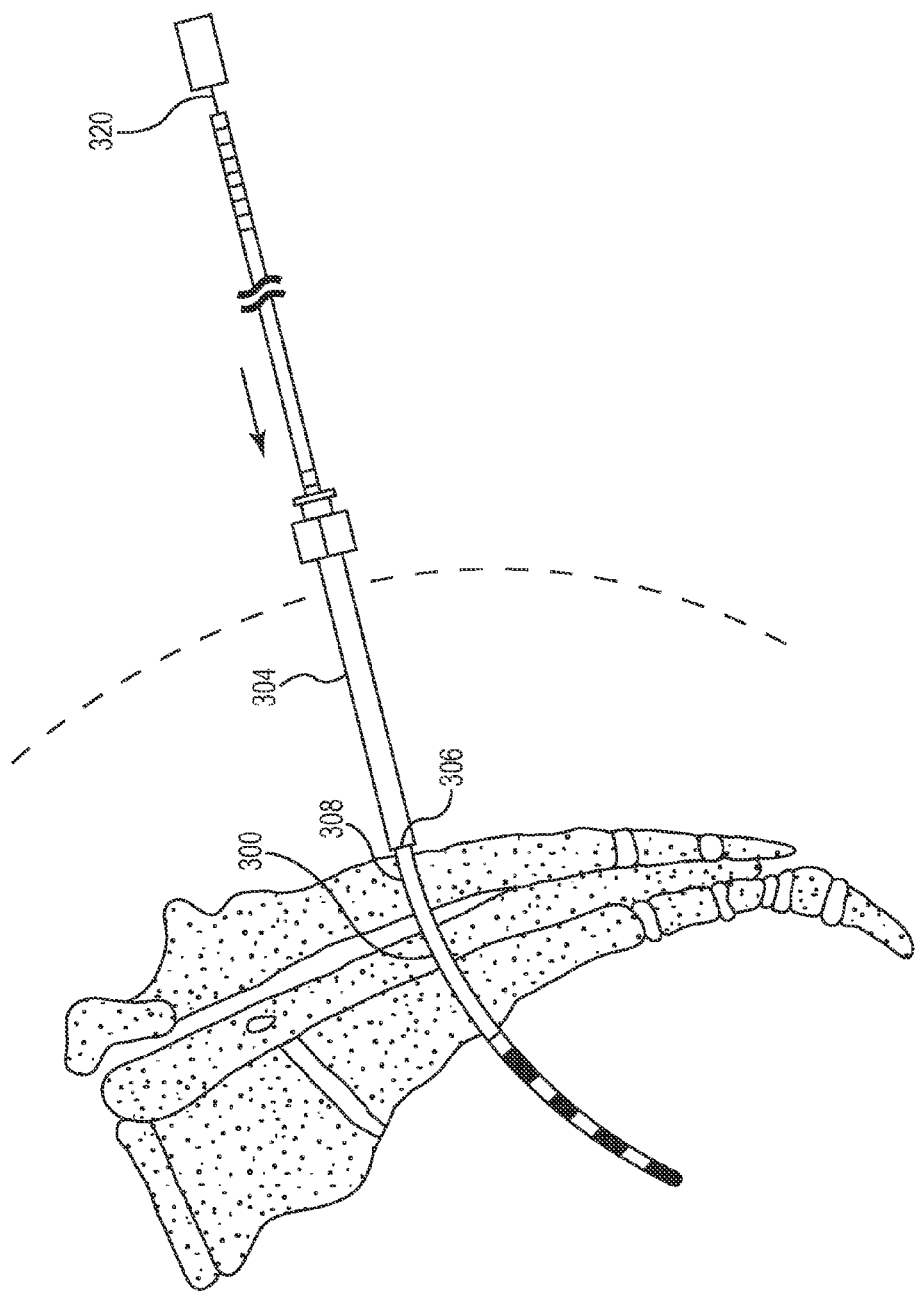

LEAD WITH BRAIDED REINFORCEMENT

FIELD

The present disclosure is directed to a method and apparatus that allows for stimulation of body tissue, particularly nerves. More specifically, this disclosure relates to an implantable medical electrical lead with a braided reinforcement. The present lead can be used with or without fixation structures to provide stability for the stimulation electrodes. Moreover, this disclosure relates to the method of implantation and anchoring of the medical electrical lead electrodes in operative relation to a selected nerve to allow for stimulation.

BACKGROUND

Implantable medical electronics devices consist of an implanted pulse generator that is used to provide electrical stimulation to certain tissues and an implantable lead or leads that are used to transmit the electrical impulse to the targeted tissues. Examples include cardiac pacemaking, and a number of related applications for cardiac rhythm management, treatments for congestive heart failure, and implanted defibrillators. Other applications for implantable pulse generators include neurostimulation with a wide range of uses such as pain control, nervous tremor mitigation, incontinent treatment, epilepsy seizure reduction, vagus nerve stimulation for clinical depression, and the like.

Despite various suture fixation devices, nerve stimulation leads can be dislodged from the most efficacious location due to stresses placed on the lead by the ambulatory patient. A surgical intervention is then necessary to reposition the electrode and affix the lead. The implantable pulse generator ("IPG") is programmed to deliver stimulation pulse energy to the electrode providing the optimal nerve response. The efficacy of the selected electrode can fade over time due to dislodgement or other causes.

Physicians spend a great deal of time with the patient under a general anesthetic placing the small size stimulation electrodes relative to the target nerves. The patient is thereby exposed to the additional dangers associated with extended periods of time under a general anesthetic. Movement of the lead, whether over time from suture release or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation that, in turn, requires consistent presence of the stimulation electrode proximate the target nerve. On the other hand, if the target nerve is too close to the electrode, inflammation or injury to the nerve can result, diminishing efficacy and possibly causing patient discomfort.

Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known in the art as exemplified by U.S. Pat. Nos. 3,902,501, 3,939,843, 4,033,357, 4,236,529, 4,269,198, 4,301,815, 4,402,328, 4,409,994, and 4,883,070, for example. Such tined leads typically employ tines that extend outwardly and proximally from a band proximal to a distal tip pace/sense electrode and that catch in natural trabecular interstices when the distal tip electrode is advanced into the atrial appendage or the ventricular apex.

Certain spinal cord stimulation leads have been proposed employing tines and/or vanes as stand-offs to urge the stimulation electrode in the epidural space toward the spinal cord as disclosed in U.S. Pat. Nos. 4,590,949 and 4,658,535, for example, and to stabilize the stimulation electrode in the epidural space as disclosed in U.S. Pat. No. 4,414,986, for example.

Stimulation leads for certain pelvic floor disorders have been proposed with a fixation mechanism that includes a plurality of tine elements arrayed in a tine element array along a segment of the lead proximal to the stimulation electrode array, such as for example in U.S. Pat. Nos. 6,999,819; 7,330,764; 7,912,555; 8,000,805; and 8,036,756. Each tine element includes a plurality of flexible, pliant, tines. The tines are configured to be folded inward against the lead body when fitted into and constrained by the lumen of an introducer.

Peripheral nerve field stimulation ("PNFS") involves delivery of stimulation to a specific peripheral nerve via one or more electrodes implanted proximate to or in contact with a peripheral nerve, such as disclosed in U.S. Pat. Publication No. 2009/0281594. PNFS may be used to deliver stimulation to, for example, the vagal nerves, cranial nerves, trigeminal nerves, ulnar nerves, median nerves, radial nerves, tibial nerves, and the common peroneal nerves. When PNFS is delivered to treat pain, one or more electrodes are implanted proximate to or in contact with a specific peripheral nerve that is responsible for the pain sensation.

Tined leads can create problems during removal or explant. In particular, the human body recognizes a lead as a foreign body and forms fibrous tissue around the lead. The fibrous tissue strengthens the engagement with the tines. If the anchoring of the tines is stronger than the lead itself, the lead may break during removal, leaving fragments behind. These fragments can migrate creating pain and increasing the risk of infection. Additional surgery is often required to remove the fragments.

BRIEF SUMMARY

The present disclosure is directed to a therapy delivery element with a braided reinforcement structure having a free end located near the connector assembly. The present therapy delivery element provides a high degree of elasticity between the connector assembly and the electrode assembly, while the high tensile strength of the braided structure dramatically reduces the risk of fracture during removal. During removal from the patient, the surgeon grasps the free end of the braided structure.

The present disclosure is directed to a therapy delivery element configured for at least partial insertion in a living body. The therapy delivery element includes a conductor assembly with a plurality of conductors. An electrode assembly is located at a distal end of the conductor assembly. The electrode assembly includes a plurality of electrodes that are electrically coupled to the conductors. A connector assembly is located at a proximal end of the conductor assembly. The connector assembly includes a plurality of electrical contacts that are electrically coupled to the conductors. The braided structure surrounds the conductor assembly. A distal end of the braided structure is attached to an electrode assembly and a free floating proximal end is located near a connector assembly. An outer tubing surrounds the braided structure. The outer tubing includes a proximal end attached to the connector assembly and a distal end attached to the braided structure near the electrode assembly or attached directly to the electrode assembly. A proximal tension force applied to the connector assembly acts substantially on the outer tubing and the conductor assembly, providing substantial axial elasticity. A proximal tension force applied to the free floating proximal end acts substantially on the braided structure to provide high tensile strength during removal.

The elongation of the outer tubing section is preferably decoupled from elongation of the braided section. A tension force applied to the free floating proximal end is preferably substantially transmitted to the electrode assembly independent of the outer tubing. A tension force applied to the free floating proximal end the therapy delivery element exhibits a percentage elongation generally corresponding to a percentage elongation of the braided structure. A tension force applied to the connector assembly exhibits a percentage elongation generally corresponding to a percentage elongation of the outer tubing and the conductor assembly.

A tension force applied to the free floating end of the braided structure provides a percent elongation in a range between about 0.5% to about 15%. The tension force applied to the free floating end of the braided structure provides a yield strength in a range between about 8 lbs. to about 15 lbs. A tension force applied to the connector assembly provides a percent elongation in a range between about 5% to about 30%. The tension force applied to the connector assembly provides a yield strength in a range between about 1 lbs. to about 7 lbs. The yield strength of the present therapy delivery element when the tension force is applied to the free floating proximal end of the braided structure is about 5 times greater than the yield strength when the tension force is applied to the connector assembly. Consequently, the present therapy delivery element combines a high level of strain relief with sufficient tensile strength to permit removal from the patient with minimal risk of fragmentation.

An axial force required to fully stretch the therapy delivery element between the connector assembly and the distal end of the outer tubing is less than about 10% of the yield strength of the therapy delivery element between the free floating proximal end and the electrode assembly.

The braided structure optionally extends substantially to a distal end of the electrode assembly. Inner tubing is optionally bonded to the braided structure to increase strength and to prevent tissue in-growth. The inner tubing optionally extends substantially to a distal end of the electrode assembly. A thermoplastic material is optionally melted into engagement with the braided structure.

At least one fixation structure is optionally attached to the therapy delivery element near the electrode assembly.

The present disclosure is also directed to a neurostimulation system including an implantable pulse generator. A therapy delivery element as discussed herein is provided. The electrical contacts on the connector assembly are configured to electrically couple with the implantable pulse generator.

The present disclosure is also directed to a method of making a therapy delivery element configured for at least partial insertion in a living body. The method includes braiding a plurality of fibers to form a braided structure with a lumen. A conductor assembly including a plurality of conductors is located in the lumen of the braided structure. An outer tubing is positioned around the braided structure and the conductor assembly. Electrodes on an electrical assembly are electrically coupled to the conductors at a distal end of the conductor assembly. Electrical connectors on a connector assembly are electrically coupled to the conductors at a proximal end of the conductor assembly. The braided structure is attached to the electrode assembly, while leaving a proximal end of the braided structure free floating in the outer tubing. A proximal end of the outer tubing is attached to the connector assembly. A distal end of the outer tubing is bonded to the braided structure at or near the electrode assembly. A proximal tension force applied to the connector assembly acts substantially on the outer tubing and the conductor assembly, and a proximal tension force applied to the proximal end of the braided structure acts substantially on the braided structure.

BRIEF DESCRIPTION OF THE DRAWINGS

FIG. 7 is a side view of a therapy delivery element with a braided reinforcement in accordance with an embodiment of the present disclosures.

FIG. 8 is a side view a connector assembly of the therapy delivery element of FIG. 7.

FIG. 9A is a side sectional view of an electrode assembly for the therapy delivery element of FIG. 7 in accordance with an embodiment of the present disclosure.

FIG. 9B is a side sectional view of an alternate electrode assembly for the therapy delivery element of FIG. 7 in accordance with an embodiment of the present disclosure.

FIG. 10 is a side sectional view of a bonding location of the outer tube to the therapy delivery element of FIG. 7 in accordance with an embodiment of the present disclosure.

FIG. 11 is a side sectional view of a proximal end of the braided reinforcement of the therapy delivery element of FIG. 7 in accordance with an embodiment of the present disclosures.

FIG. 12A is a side view of an alternate therapy delivery element with a braided reinforcement in accordance with an embodiment of the present disclosures.

FIG. 12B is a side sectional view of a proximal end of the braided reinforcement of the therapy delivery element of FIG. 12A in accordance with an embodiment of the present disclosures.

FIG. 13 illustrates a portion of method of implanting a therapy delivery element in accordance with an embodiment of the present disclosure.

DETAILED DESCRIPTION OF SOME EMBODIMENTS

The description that follows highlights spinal cord stimulation (SCS) system, the treatment of pelvic floor disorders, and peripheral nerve field stimulation (PNFS). However, it is to be understood that the disclosure relates to any type of implantable therapy delivery system with one or more therapy delivery elements with one or more electrodes or sensors. For example, the present disclosure may be used as part of a pacemaker, a defibrillator, a cochlear stimulator, a retinal stimulator, a stimulator configured to produce coordinated limb movement, a cortical stimulator, a deep brain stimulator, microstimulator, or in any other neural stimulator configured to treat sleep apnea, shoulder sublaxation, headache, etc.

In another embodiment, one or more of the therapy delivery elements may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
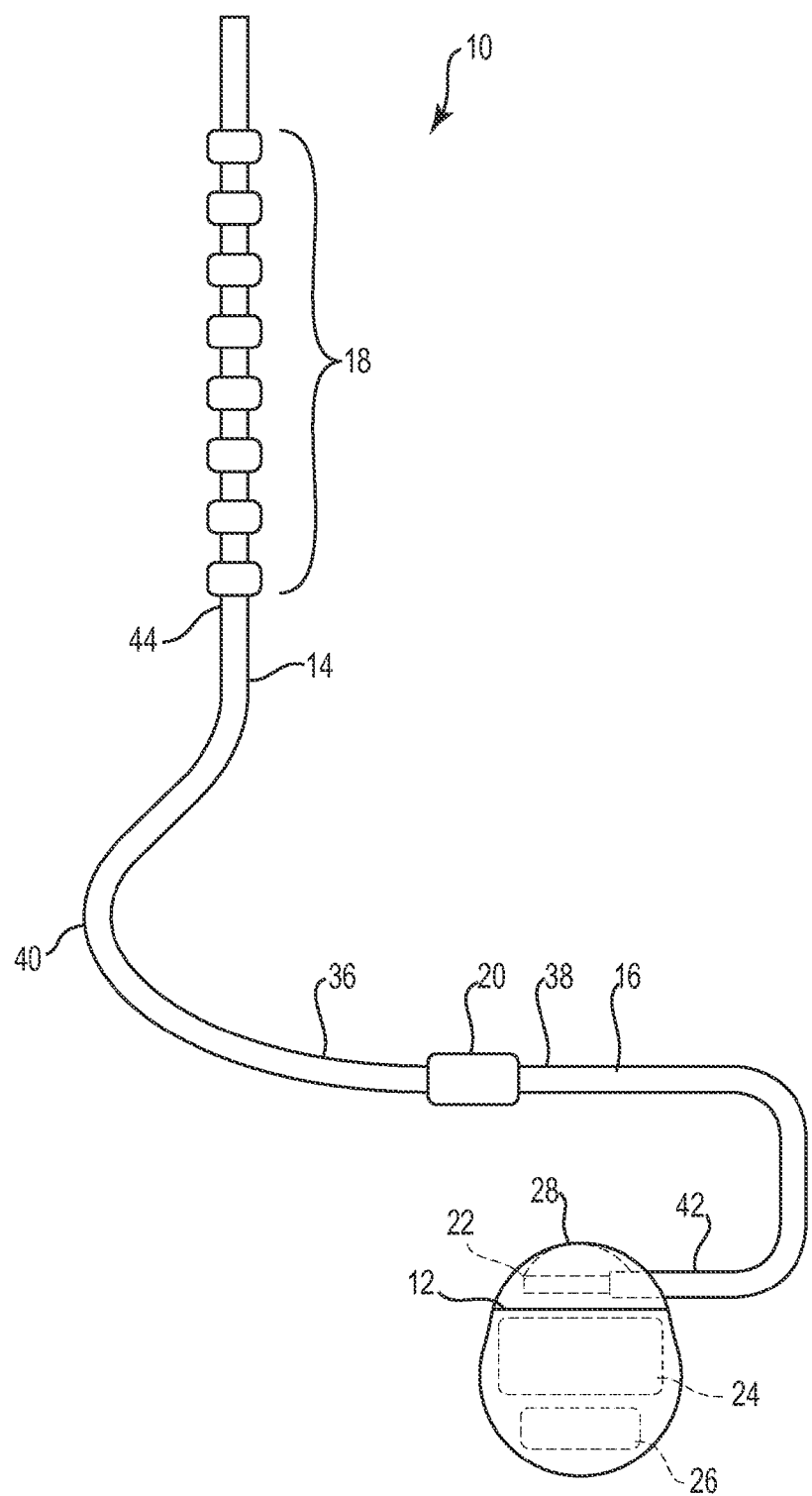
FIG. 1 is a schematic illustration of a therapy delivery system.

FIG. 1 illustrates a generalized therapy delivery system 10 that may be used in stimulation applications. The therapy delivery system 10 generally includes an implantable pulse generator 12 ("IPG") ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2A:
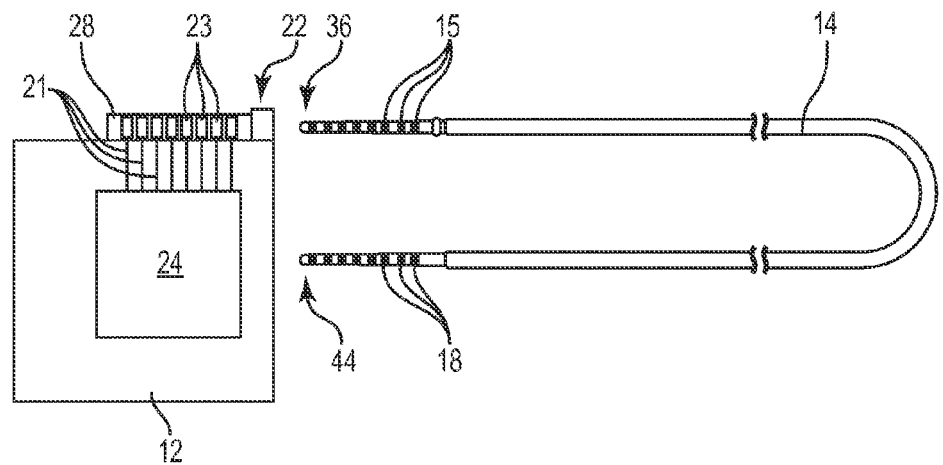
FIG. 2A is a schematic illustration of an implantable pulse generator and a therapy delivery element in accordance with an embodiment of the present disclosure.

FIG. 2A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 2A and 2B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configured to independently deliver electrical impulses to each of the electrodes 18.

Figure 2B:
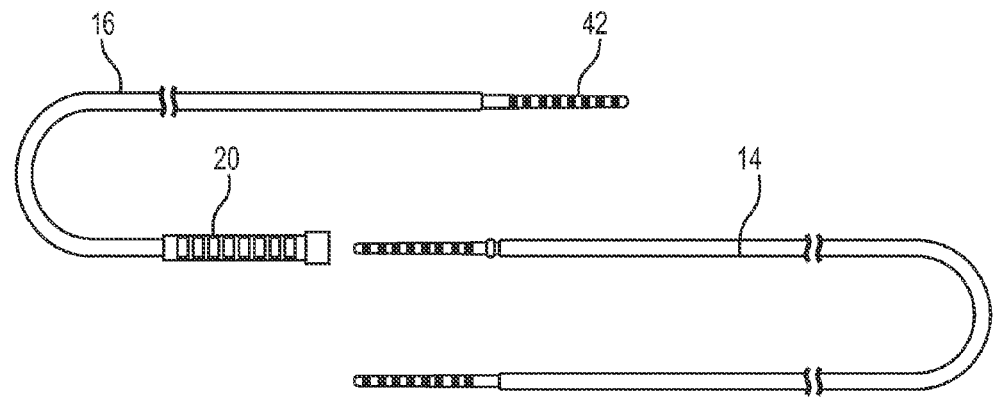
FIG. 2B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 2B. The connector 20 at the distal end 38 of the lead extension 16 preferably includes a plurality of the contacts 23 configured in a manner similar to the connector assembly 22.

Figure 3:
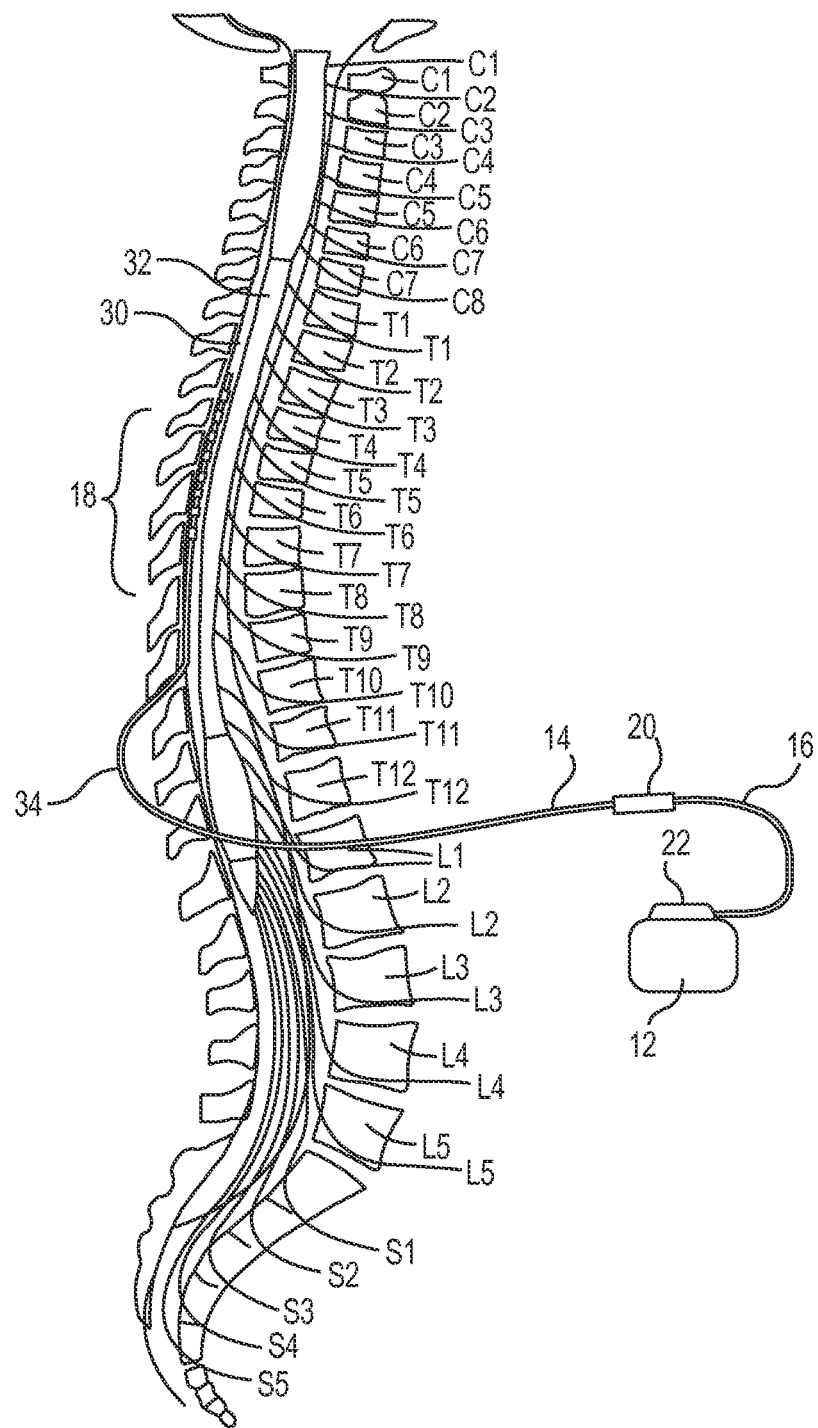
FIG. 3 is a schematic illustration of a therapy delivery system for spinal cord stimulation in accordance with an embodiment of the present disclosure.

FIG. 3 illustrates the therapy delivery element 14 used for spinal cord stimulation (SCS) implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as the proximate sacral nerves.

Figure 4:
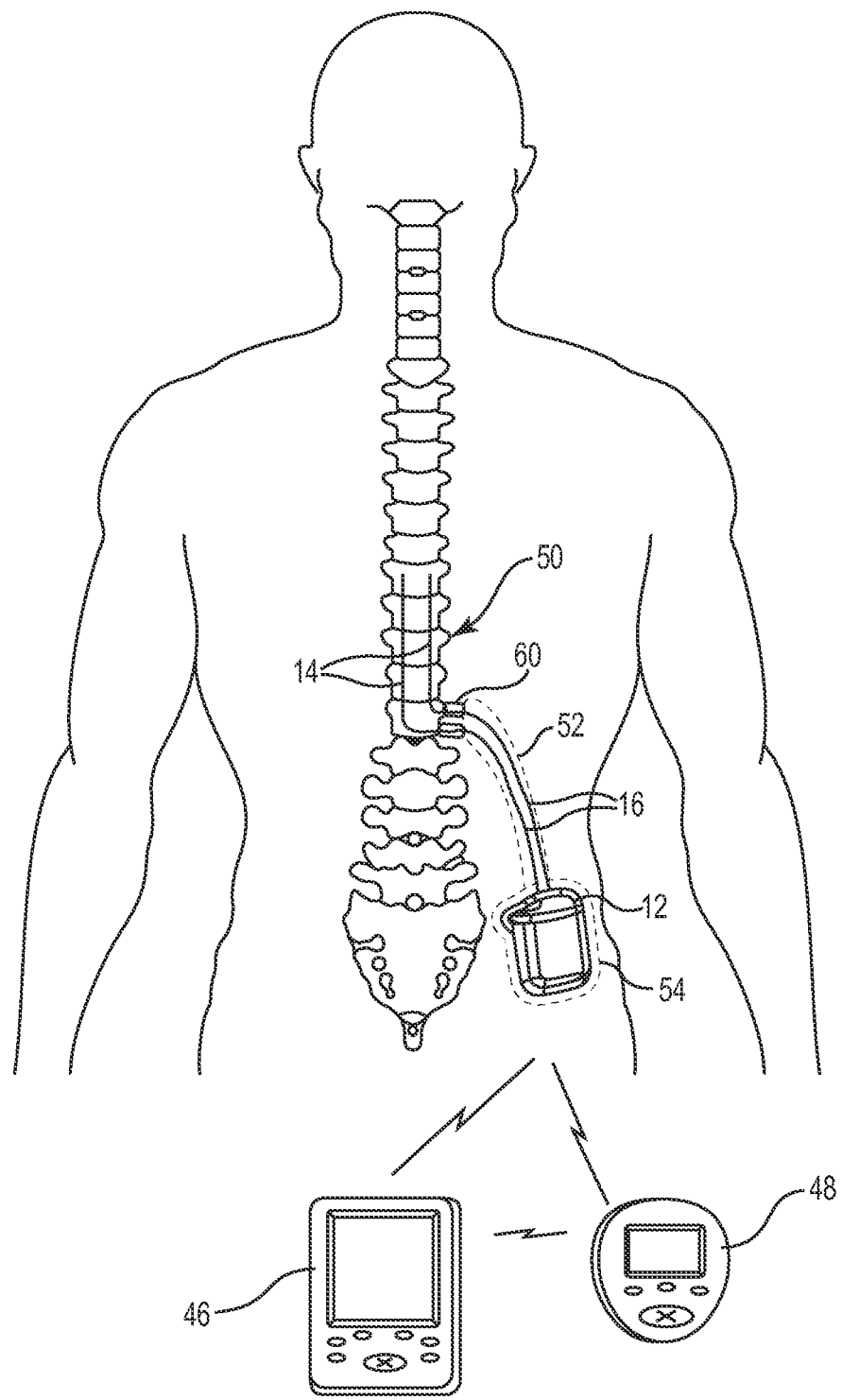
FIG. 4 is an alternate illustration of an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 4. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 4, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 5:
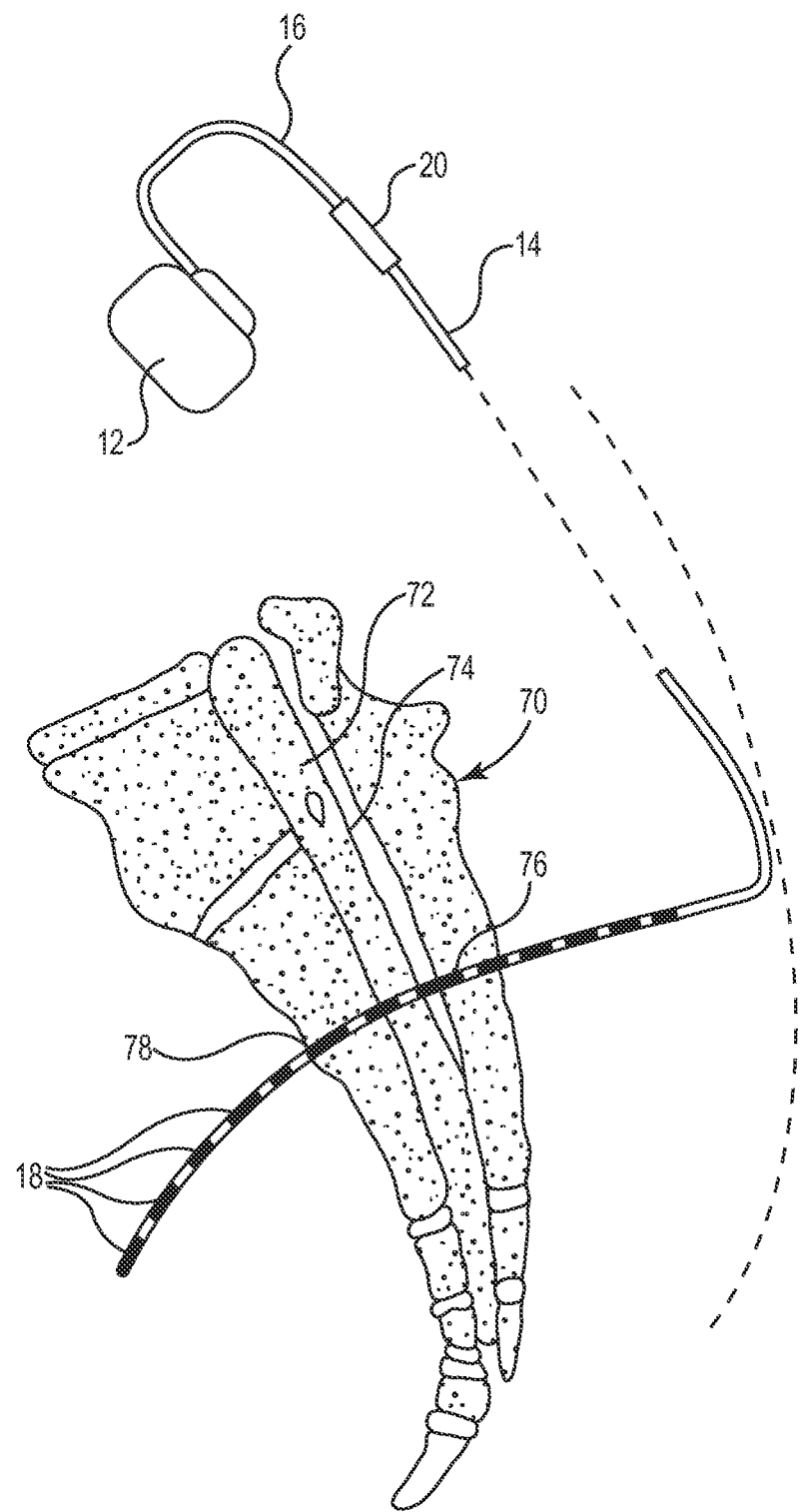
FIG. 5 is a schematic illustration of a therapy delivery system for treating pelvic floor disorders in accordance with an embodiment of the present disclosure.

FIG. 5 illustrates the therapy delivery element 14 used for pelvic floor disorders such as, urinary incontinence, urinary urge/frequency, urinary retention, pelvic pain, bowel dysfunction (constipation, diarrhea), erectile dysfunction, are bodily functions influenced by the sacral nerves. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles 72 within the sacrum 70. The sacrum 70, generally speaking, is a large, triangular bone situated at the lower part of the vertebral column, and at the upper and back part of the pelvic cavity. The spinal canal 74 runs throughout the greater part of the sacrum 70. The sacrum is perforated by the posterior sacral foramina 76 and anterior sacral foramina 78 that the sacral nerves 70 pass through.

Specifically, urinary incontinence is the involuntary control over the bladder that is exhibited in various patients. The therapy delivery element 14 is percutaneously implanted through the foramina 76, 78 of the sacral segment S3 for purposes of selectively stimulating the S3 sacral nerve 72. Stimulation energy is applied through the lead 14 to the electrodes 18 to test the nerve response. The electrodes 18 are moved back and forth to locate the most efficacious location, and the lead 14 is then secured by suturing the lead body to subcutaneous tissue posterior to the sacrum 70 and attached to the output of a neurostimulator IPG 12.

Figure 6:
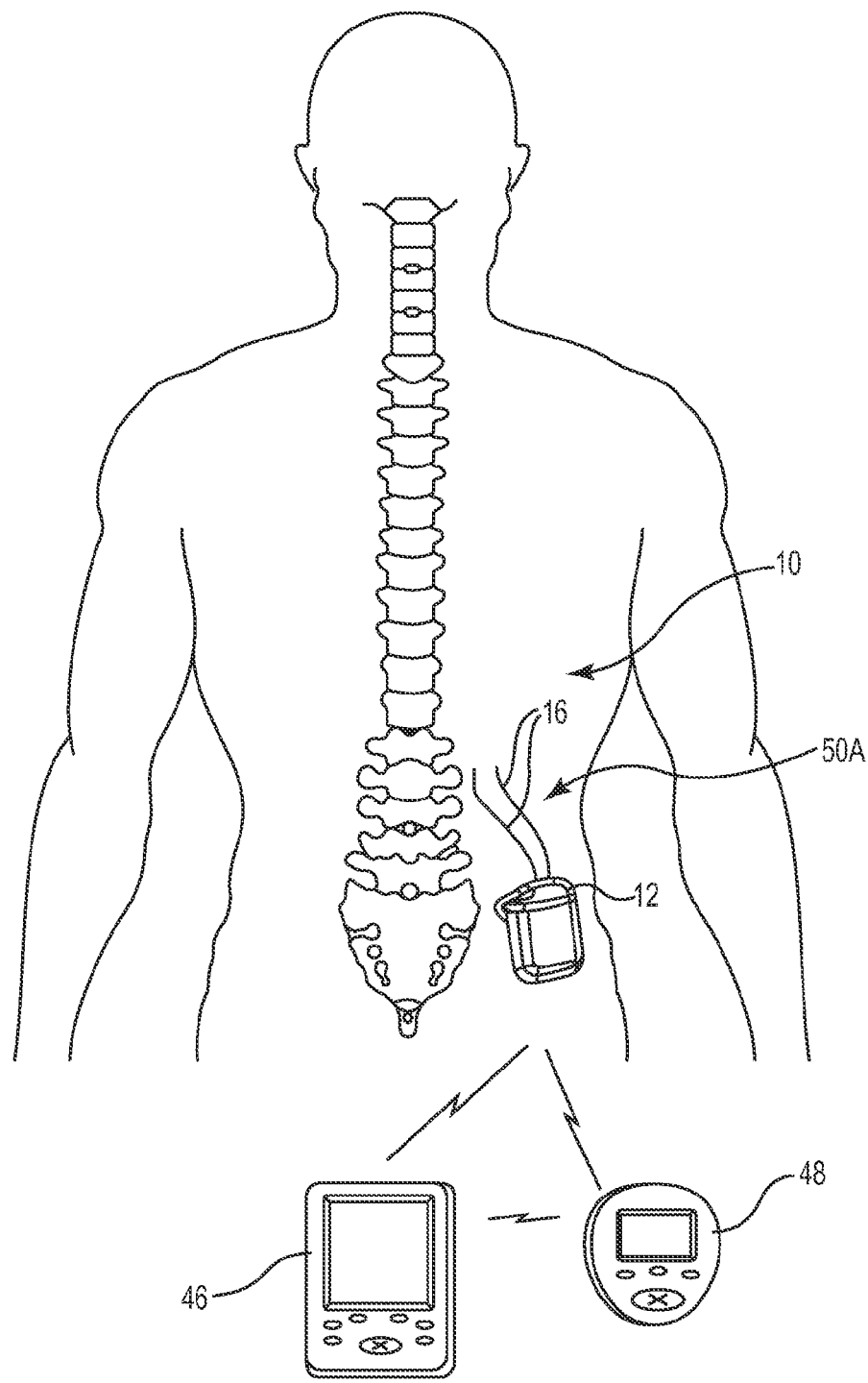
FIG. 6 is a schematic illustration of a therapy delivery system for peripheral nerve stimulation in accordance with an embodiment of the present disclosure.

FIG. 6 illustrates the therapy delivery element 14 used for delivering peripheral nerve field stimulation (PNFS) to a patient. Therapy delivery element 14 delivers PNFS from the implantable pulse generator 12 to the tissue of patient at target location 50A where patient experiences pain. Clinician programmer 46 and patient programmer 48 may communicate via wireless communication with the implantable pulse generator 12.

Therapy delivery element 14 may be implanted within or between, for example, intra-dermal, deep dermal, or subcutaneous tissue of patient at the location 50A where patient experiences pain. Subcutaneous tissue includes skin and associated nerves, and muscles and associated nerves or muscle fibers. In the illustrated example, location 50A is a region of the lower back. In other examples, the therapy delivery element 14 may extend from implantable pulse generator 12 to any localized area or dermatome in which patient experiences pain, such as various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis.

FIGS. 7 and 8 are side views of a therapy delivery element 100 with a reinforcing braided structure 102 (see FIG. 9) in accordance with an embodiment of the present disclosure. The therapy delivery element 100 includes a connector assembly 104 at proximal end 106 and electrode assembly 108 at distal end 110. The connector assembly 104 includes a plurality of electrical connectors 122 and the electrode assembly 108 includes a plurality of electrodes 124. A conductor assembly 126 (see FIG. 10) extends through lumen 128 of lead body 130 to electrically couple the electrical connectors 122 to the electrodes 124. In the illustrated embodiment, the electrode assembly 108 and/or the connector assembly 104 are discrete molded structures. In an alternate embodiment, the electrodes 124 and/or the electrical connectors 122 are attached directly to the lead body 130.

The therapy delivery element 100 optionally includes fixation structures 136, such as symmetrical and asymmetrical protrusions. Various fixation structures 136 suitable for the present therapy delivery element 100 are disclosed in commonly assigned U.S. patent application Ser. Nos. 13/537,494, pending, entitled Braided Lead with Embedded Fixation Structures, filed Jun. 29, 2012 and 13/537,341, pending, entitled Lead Positioning and Finned Fixation System, filed Jun. 29, 2012, which are hereby incorporated by reference.

The braided structure 102 preferably extends along braid section 112 from about the distal end 110 to location 114 near the proximal end 106. The location 114 is preferably sufficiently close to the proximal end 106 so as to be accessible through the same incision that provides access to the implantable pulse generator 12. The proximal section 132 between the location 114 and the connector assembly 104 typically has a length of between about 0.5 inches and about 5.0 inches.

In the preferred embodiment, outer tubing 116 extends along outer tubing section 118 from about the connector assembly 104 to a connection location 120 located along braid section 112. The outer tubing section 118 is typically within about 2.5 inches or less from the electrode assembly 108. In an alternate embodiment, the connection location 120 is located on the electrode assembly 108 so that the outer tubing 116 extends substantially the entire length 115 of the lead body 130.

The braided structure 102 has a lower percent elongation and greater resistance to axial deformation than the outer tubing 116, which provides tensile reinforcement for the therapy delivery element 100 between the location 114 and the distal end 110. If the therapy delivery element 100 is grasped at the location 114, it will exhibit a tensile strength corresponding to at least the tensile strength of the braided structure 102.

On the other hand, the outer tubing 116 has a higher percent elongation and lower resistance to axial deformation than the braided structure 102, which provides greater stretchability for the therapy delivery element 100 between the connector assembly 106 and the location 120. Along proximal section 132 near the connector assembly 104 only the outer tubing 116 covers the conductor assembly 126. If the tension force 134 is applied to the connector assembly 104, such as may occur when is implanted in a patient, the therapy delivery element 100 exhibits a percentage elongation generally corresponding to the percentage elongation of the outer tubing 116 and the conductor assembly 126.

Maximizing the length of the outer tubing section 118 maximizes the percentage elongation of the present therapy delivery element 100. By decoupling the outer tubing 116 from the braided structure 102, the present therapy delivery element 100 provides both high percent elongation and high tensile reinforcement.

The braided structure 102 preferably has a percent elongation in a range between about 0.5% and about 15.0%, but yield strength in a range between about 8 lbs. and about 15 lbs. The outer tubing 116, on the other hand, preferably has a percent elongation in a range between about 5% and about 30%, but a yield strength in a range between about 1 lbs. and about 7 lbs. The axial force required to fully stretch the therapy delivery element 100 between the connector assembly 104 and the location 120 is preferably less than about 10% of the yield strength of the braided structure between the location 114 and the electrode assembly 108. The yield strength of the present therapy delivery element 100 when the tension force 134 is applied to the free floating proximal end 180 of the braided structure 102 (see FIG. 11) is about 2 times to about 15 times, and more preferably about 5 times greater than, the yield strength when the tension force 134 is applied to the connector assembly 104. As a result, the therapy delivery element 100 combines both a high level of strain relief with a high tensile strength during extraction from the patient.

FIG. 9A is a side sectional view of one embodiment of the electrode assembly 108 of FIG. 7. Braided structure 102 preferably extends though lumen 150 of the electrode assembly 108 to near the distal end 110. The braided structure 102 is preferably bonded to the electrode assembly 108 along inside surface 156 of the lumen 150. As used herein "bonded" or "bonding" refers to adhesive bonding, solvent bonding, ultrasonic welding, heat shrinkage, compressive coupling, thermal bonding, mechanical interlocks, and a variety of other techniques. The braided structure 102 includes lumen 152 sized to receive the conductor assembly 126 (see FIG. 10), allowing the individual conductors 154 to be electrically coupled to the electrodes 124.

The braided structure 102 includes a plurality of fibers 170. The braided structure 102 is preferably an axial braid, although a variety of other braid patterns or woven structures may be used. As used herein, "braid" or "braided" refers to structures formed by intertwining or weaving three or more strands or fibers of a flexible material. Braids are preferred because of high tensile strength and good radial flexibility. The braided structure 102 reinforces the lead body 130 during ex-plant without losing flexibility. Another advantage of the braided structure 102 is that braided structure 102 necks down when a tensile load is applied. The reduced cross-sectional diameter of the braided structure 102 during ex-plant facilitates removal and promotes disengagement from the surrounding tissue.

The fibers 170 are preferably a bio-compatible polymeric material, such as for example, polyethylene terephthalate (PET), Nylon, polyether ether ketone (PEEK), polyproylene, high-performance polyethylenes, bioabsorbale polymers, such as polyglutamic acid (PGA), poly-L-lactide (PLLA), or polycaprolactone (PCL), urethane, silicone, Nitinol, stainless steel, MP35N, titanium, or any combination of these materials. Any number of discrete fibers 170 can be used in the braided structure 102, but typically there are about 4 to about 16 fibers. In one embodiment, some portion of the fibers 170 run clockwise and the remainder run counterclockwise within the braided structure 102.

The fibers 106 are preferably a mono-filament with a diameter in a range of about 0.001 inches to about 0.006 inches. Selection of the fibers 170 depends on a variety of variables, such as for example, the desired diameter and/or overall length of the lead body 130. In one embodiment, the braided structure 102 includes about 12 fibers 170 made from PET, each having a diameter of about 0.004 inches.

In another embodiment, some of the fibers 170 are made from a conductive material, like copper, platinum, MP35N, or silver, to provide shielding and grounding for the resulting therapy delivery element. For example, some of the fibers 170 are optionally made from a conductive material to provide shielding to the lead. In embodiments where the braided structure 102 includes metal wires, the tensile strength of the therapy delivery element 100 increases at least about 30% to about 50%.

In the illustrated embodiment, braided structure 102 includes tubing 160 that prevents tissue in-growth around fibers 170. The tubing 160 is preferably bonded or reflowed into the braided structure 102 to increase the overall strength of the therapy delivery element 100. In the illustrated embodiment, distal end 162A of the tubing 160 is bonded to electrode assembly 108 at location 164.

The tubing 160 extends in proximal direction 155 to at least the location 120 where the outer tubing 116 begins. As a result, the braided structure 102 is completely isolated from potential tissue in-growth. In another embodiment, the tubing 160 extends the full length of the braided structure 102 to the location 114.

The tubing 160 increases the yield strength of the braided structure 102 by at least 10%. The tubing 160 also serves to protect the conductor assembly 126 from abrasion that might occur when interacting with the fibers 170 of the braided structure 102.

FIG. 9B is a side sectional view of an alternate embodiment in which the tubing 160 extends into the lumen 150 of the electrode assembly 108. In the illustrated embodiment, distal end 162B of the tubing 160 is located adjacent the distal end 110 of the electrode assembly 108. In the embodiment of FIG. 9B, the outer tubing 116 extends to the electrode assembly 108. The outer tubing 116 is bonded to the electrode assembly 108 at the location 120.

FIG. 10 is a side sectional view of the lead body 130 at the location 120 where the outer tubing 116 attaches to the braided structure 102 in accordance with an embodiment of the present disclosure. In the illustrated embodiment, the outer tubing 116 is bonded to the tubing 160 containing the braided structure 102 at the location 120. In another embodiment, the outer tubing 116 compressively engages the braided structure 102, such as by heat shrinkage, compressive force, and the like.

In one embodiment, the outer tubing 116 has an inner diameter 172 greater than outer diameter 174 of the braided structure 102 (including the tubing 160), creating gap 173. The gap 173 minimizes friction between the outer tubing 116 and the inner tubing 160 and the braided structure 102. Assuming minimal friction, the gap 173 permits the outer tubing 116 to stretch substantially independently from the braided structure 102 and the inner tubing 160 during elongation of the therapy delivery element 100. When tensile load 134 is applied to the therapy delivery element 100, the outer tubing 116 necks-down and the gap 173 is reduces or substantially closes.

The tubing 116 and 160 can be constructed from a variety of bio-compatible polymeric materials, such as for example, polyproylene, high-performance polyethylenes, PLLA, or PCL, urethanes such as Tecothane®, silicone, or combination thereof.

Conductor assembly 126 is located in the lumen 152 of the braided structure 102 to electrically couple the electrical connectors 122 to the electrodes 124. The conductor assembly 126 preferably has an outer diameter 142 that is less than inner diameter 144 of the braided structures 102, creating gap 145. Assuming minimal friction between the conductor assembly 126 and the braided structure 102 and tubing 160, the gap 145 permits the conductor assembly 126 to stretch substantially independently of the braided structure 102 and the tubing 160.

The conductor assembly 126 includes one or more conductors 154 (see e.g., FIG. 10) extending through the lumen 128 from the electrode assembly 108 to the connector assembly 104. Typically there is a one-to-one correlation between the number of electrodes 124, connectors 122 and conductors 154. For example, if there are eight electrodes 124 and eight connectors 122, the conductor assembly 126 includes eight conductors 154. As used herein, "conductor assembly" refers to one or more insulated or un-insulated conductive wires or cables arranged in a variety of configurations, including straight, coiled, braided, and the like, that electrically couple electrodes at one end of a lead body to connectors at an opposite end. Alternate coil configurations for use in the conductor assembly 126 are disclosed in commonly assigned U.S. application Ser. No. 13/045,908, now published as U.S. Patent Application Publication No. 2012/0232625, entitled Implantable Lead with Braided Conductors, filed Mar. 11, 2011; and U.S. application Ser. No. 13/220,913, now published as U.S. Patent Application Publication No. 2013/0053864, entitled Lead Body with Inner and Outer Co-Axial Coils, filed Aug. 30, 2011, which is hereby incorporated by reference.

The conductors 154 can in include single conductive element, a plurality of conductive wires, or a combination thereof. For example, each conductor 154 optionally includes a plurality of un-insulated conductive wires twisted in a rope-like configuration or cable. Each individual cable is insulated. The individual wires can be homogenous or a multi-layered structure. For example, the core can be silver or copper and the outer layer can be a nickel-cobalt-chromium-molybdenum alloy, such as for example, MP35N. According to one embodiment, the cable included seven 0.005 inch diameter, silver core MP35N conductors arranged in a 1×7 configuration and covered with an ETFE (ethylene tetrafluoroethylene) coating.

The conductor assembly 126 preferably includes lumen 158 configured to receive a stylet wire 320 that increases the rigidity and column strength of the therapy delivery element 100 during implantation (see FIG. 13). Suitable stylets are disclosed in commonly assigned U.S. patent application Ser. No. 13/222,018, now published as U.S. Patent Application Publication No. 2013/0053865, entitled Adjustable Wire Length Stylet Handle, filed Aug. 31, 2011, and in U.S. Pat. Nos. 6,214,016; 6,168,571; 5,238,004; 6,270,496 and 5,957,966, all of which are hereby incorporated by reference.

FIG. 11 is a side sectional view of unattached or free floating proximal end 180 of the braided structure 102 and the tubing 160 at the location 114 in accordance with an embodiment of the present disclosure. Only the outer tubing 116 and the conductor assembly 126 extend from the location 114 continue in the proximal direction 155 to the connector assembly 104, without the braided structure 102 or the tubing 160.

The present structure decouples the elongation of the outer tubing 116 and conductor assembly 126 from the elongation of the braided structure 102. In particular, the free floating distal end 180 permits the conductor assembly 126 and outer tubing 116 to elongate independently from the braided structure 102.

As discussed herein, the outer tubing section 118 exhibits a significantly greater percent elongation than the braided section 112. If a tension force 134 is applied to the connector assembly 104, the therapy delivery element 100 exhibits a percentage elongation generally corresponding to a percentage elongation of the outer tubing 116 and the conductor assembly 126. The tension force 134 on the connector assembly 104 is carried primarily by the outer tubing 116 and the conductor assembly 126. The present therapy delivery element 100 provides a percent elongation in a range of between about 10% to about 30%.

On the other hand, if the tension force 134 is applied to the free floating proximal end 180, the therapy delivery element 100 exhibits a percentage elongation generally corresponding to a percentage elongation of the braided structure 102 and the tubing 160. The tension force 134 applied to the free floating proximal end 180 is substantially transmitted to the electrode assembly 108 independent of the outer tubing 116, greatly reducing the risk of breakage during removal from the patient.

During removal of the therapy delivery element 100 from the living body, the surgeon makes an incision near the implantable pulse generator 28 to expose the therapy delivery element 100. Since the braided section 112 extends to a location 114 near the connector assembly 104, the braided structure 102 is visible to the surgeon. The surgeon grasps the therapy delivery element 100 along the braided section 112 and pulls. Most of the tension force 134 is carried by the braided structure 102 and the tubing 160. The higher tensile properties of the braided structure 102 are transmitted to the electrode assembly 108, greatly reducing the risk of breaks during removal from the patient.

The braided structure 102 reinforces the therapy delivery element 100 during removal, without compromising compliance. By not running the braided structure 102 the entire length of the therapy delivery element 100, however, the therapy delivery element 100 exhibits a percent elongation far greater than conventional braided leads.

FIGS. 12A and 12B illustrate an alternate therapy delivery element 200 without the outer tubing 116 of FIG. 7, in accordance with an embodiment of the present disclosure. The therapy delivery element 200 include braided structure 202 surrounded by tubing 204, as illustrated in FIG. 9A. The tubing 204 extends from connector assembly 206 to electrode assembly 208 to protect the conductor assembly 218 and the prevent tissue in-growth. The braided structure 202, however, extends from the connection location 214 to near the distal end 212.

As best illustrated in FIG. 12B, the braided structure 202 terminates at the location 214, but the tubing 204 continues to the connector assembly 206, protecting the conductor assembly 218. The braided structure 202 provides tensile reinforcement for the therapy delivery element 200 between the connection location 214 and the distal end 212. Along proximal section 220 near the connector assembly 206, however, only the tubing 204 covers the conductor assembly 218.

The outer tubing section 220 exhibits a significantly greater percent elongation than the braided section 210. If a tension force 222 is applied to the connector assembly 206, the therapy delivery element 200 exhibits a percentage elongation generally corresponding to a percentage elongation of the outer tubing section 220 and the conductor assembly 218. The tension force 222 on the connector assembly 206 is carried primarily by the outer tubing section 220 and the conductor assembly 218.

On the other hand, if the tension force 222 is applied at the location 214, the therapy delivery element 200 exhibits a percentage elongation generally corresponding to a percentage elongation of the braided structure 202 and the tubing 204. The tension force 222 applied at the location 214 is substantially transmitted to the electrode assembly 208 independent of the more elastic outer tubing section 220, greatly reducing the risk of breakage during removal from the patient.

To remove the therapy delivery element 200 from a living body, the surgeon grasps the therapy delivery element 200 along the braided section 210 and pulls. The braided structure 202 reinforces the therapy delivery element 200 during removal, without compromising compliance. By not running the braided structure 202 the entire length of the therapy delivery element 200, however, the therapy delivery element 200 exhibits a percent elongation far greater than conventional braided leads.

FIG. 13 illustrates one embodiment of a therapy delivery element 300 in sacral nerve in accordance with an embodiment of the present disclosure. The therapy delivery element 300 and the fixation structures 302 (see FIG. 14) are disposed within introducer 304. The introducer 304 is advanced percutaneously at a selected angle until the introducer distal end 306 is disposed at the selected foramen 308. The therapy delivery element 300 may be inserted near any of the sacral nerves including the S1, S2, S3, or S4, sacral nerves accessed via the corresponding foramen depending on the necessary or desired physiologic response.

In one embodiment, the advancement of the introducer 304 can be accomplished separately over a guide wire previously percutaneously advanced from the skin incision into the foramen to establish the angle of advancement. In yet another embodiment, a multi-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately result in the introducer 304 at the location of FIG. 13. The therapy delivery element 300 is optionally stiffened by stylet 320 disposed in the lumen.

Figure 14:
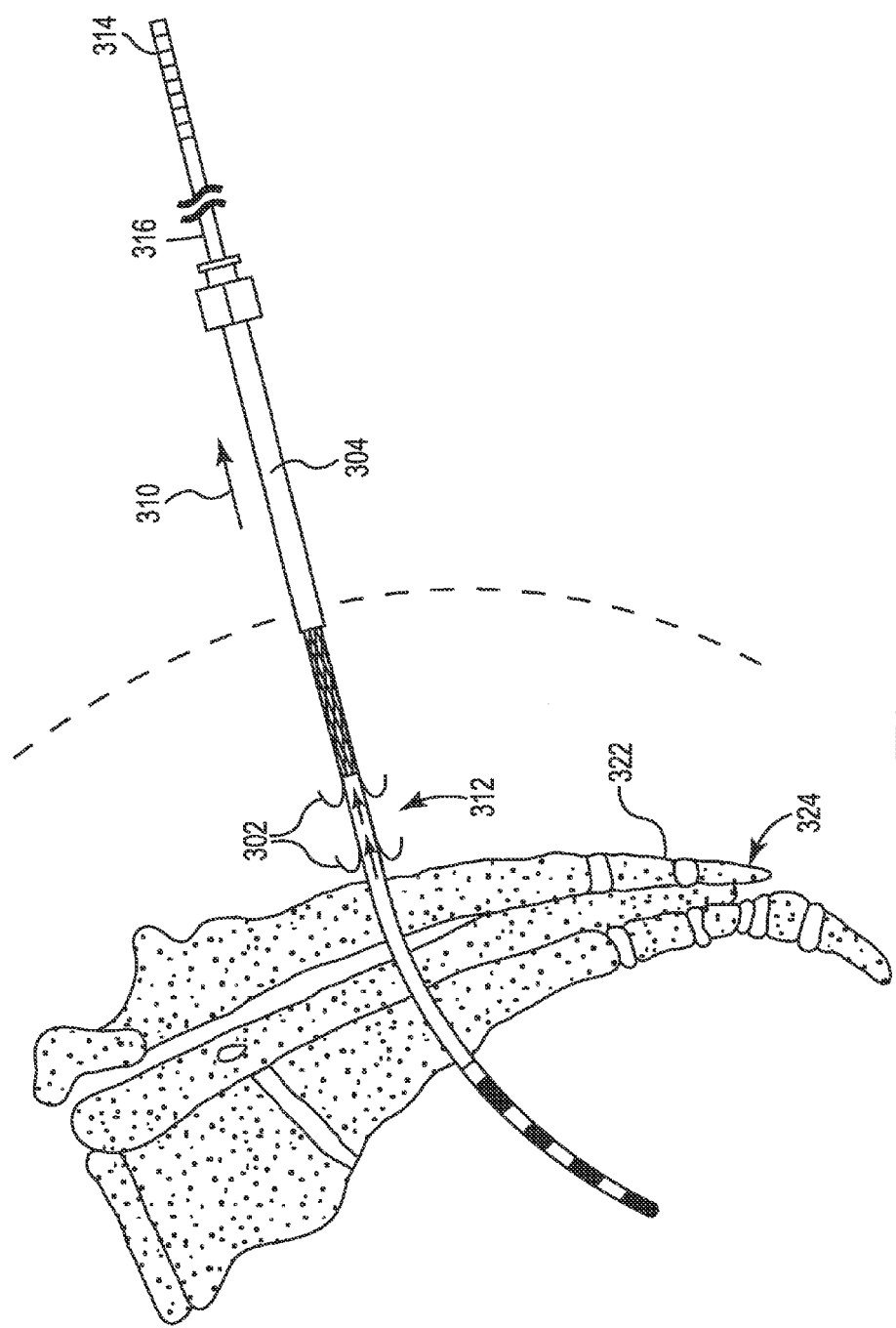
FIG. 14 illustrates a portion of a method of implanting a therapy delivery element in accordance with an embodiment of the present disclosure.

As illustrated in FIG. 14, the introducer 304 is retracted proximally in direction 310 after electrical testing of the therapy delivery element 300. The fixation structures 302 are released from the introducer 304 and engage with surrounding subcutaneous tissue 312. The fixation structures 302 preferably engage with the muscle tissue located along posterior surface 322 of the sacrum 324. In one embodiment the fixation structures 302 can be seen under fluoroscopy to allow the physician to verify that the fixation structures 302 are deployed. As shown in FIG. 5, the proximal portion 314 of the lead body 316 is bent and implanted through a subcutaneously tunneled path to the implantable pulse generator 12.

Figure 15:
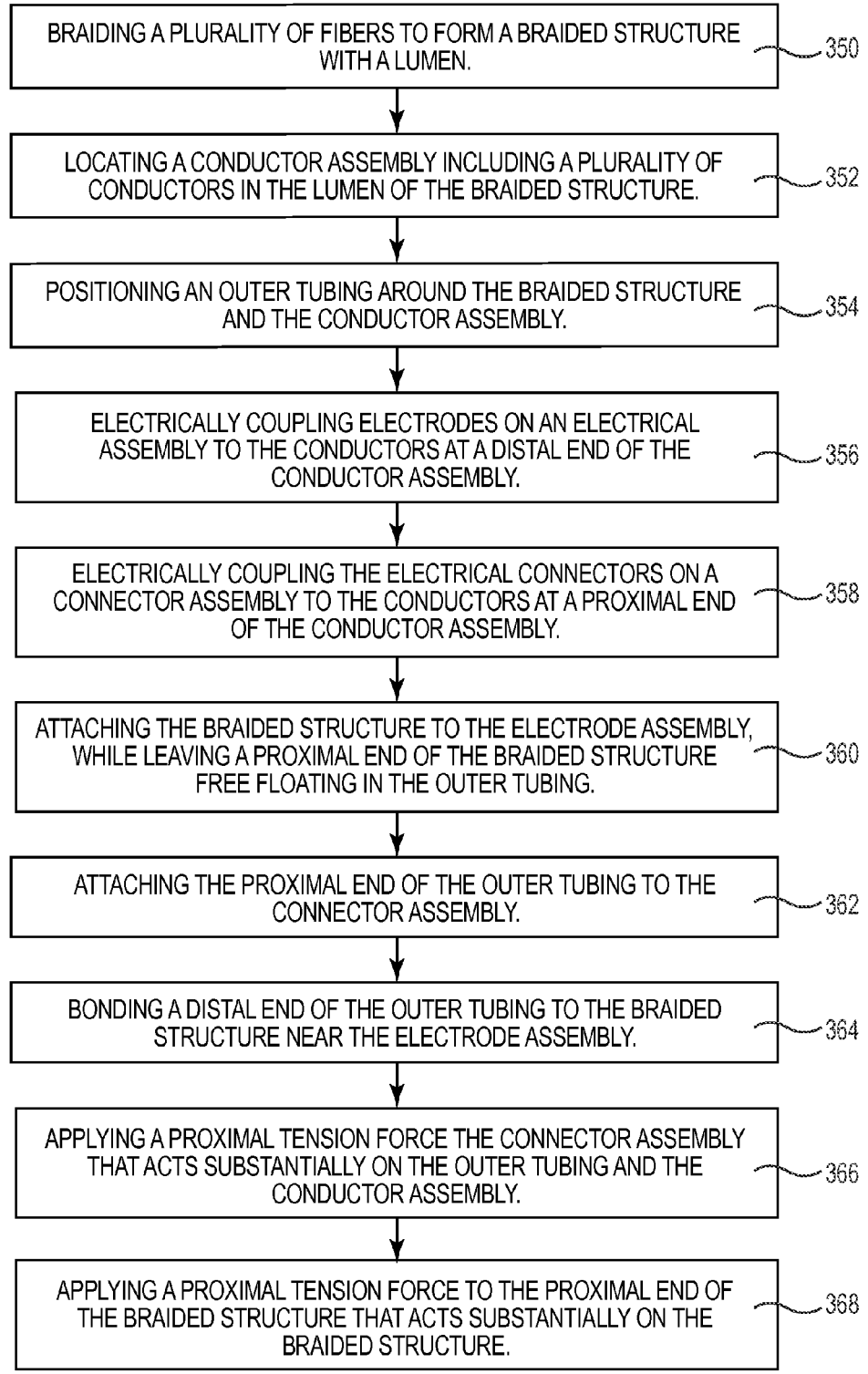
FIG. 15 is a flow chart of a method of making a therapy delivery element in accordance with an embodiment of the present disclosure.

FIG. 15 is a flow chart directed to a method of making a therapy delivery element configured for at least partial insertion in a living body according to an embodiment of the present disclosure. The method includes braiding a plurality of fibers to form a braided structure with a lumen (350). A conductor assembly including a plurality of conductors is located in the lumen of the braided structure (352). An outer tubing is positioned around the braided structure and the conductor assembly (354). Electrodes on an electrical assembly are electrically coupled to the conductors at a distal end of the conductor assembly (356). Electrical connectors on a connector assembly are electrically coupled to the conductors at a proximal end of the conductor assembly (358). The braided structure is attached to the electrode assembly, while leaving a proximal end of the braided structure free-floating in the outer tubing (360). A proximal end of the outer tubing is attached to the connector assembly (362). A distal end of the outer tubing is bonded to the braided structure near the electrode assembly (364). A proximal tension force applied to the connector assembly acts substantially on the outer tubing and the conductor assembly (366). A proximal tension force applied to the proximal end of the braided structure acts substantially on the braided structure (368).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A therapy delivery element configured for at least partial insertion in a living body, the therapy delivery element comprising:
   a conductor assembly comprising a plurality of conductors;
   an electrode assembly located at a distal end of the conductor assembly, the electrode assembly comprising a plurality of electrodes that are electrically coupled to the conductors;
   a connector assembly located at a proximal end of the conductor assembly, the connector assembly comprising a plurality of electrical contacts that are electrically coupled to the conductors;
   a plurality of fibers comprising a braided structure surrounding the conductor assembly along a braided section, the braided structure comprising a distal end attached to the electrode assembly and a free floating proximal end located near the connector assembly; and
   an outer tubing surrounding the braided structure along an outer tubing section, the outer tubing comprising a proximal end attached to the connector assembly and a distal end attached to the braided structure near the electrode assembly or to the electrode assembly, wherein the free floating proximal end of the braided structure is unattached to, but disposed within, the outer tubing, and wherein:
      with a proximal tension force applied to the connector assembly, an elongation of the therapy delivery element substantially corresponds to an elongation of the outer tubing and the conductor assembly;
      with the proximal tension force applied to the free floating proximal end, the elongation of the therapy delivery element substantially corresponds to an elongation of the braided structure; and
      the elongation of the therapy delivery element with the proximal tension force applied to the connector assembly is greater than the elongation of the therapy delivery element with the proximal tension force applied to the free floating proximal end.

2. The therapy delivery element of claim 1, wherein the outer tubing section is configured to be elongatable independently of the braided section.

3. The therapy delivery element of claim 1, wherein a tension force applied to the free floating proximal end is substantially transmitted to the electrode assembly independent of the outer tubing.

4. The therapy delivery element of claim 1, wherein a tension force applied to the connector assembly exhibits a percentage elongation generally corresponding to a percentage elongation of the outer tubing and the conductor assembly.

5. The therapy delivery element of claim 1, wherein, with the tension force applied to the free floating end of the braided structure, the therapy delivery element includes a percent elongation in a range between about 0.5% to about 15%.

6. The therapy delivery element of claim 1, wherein, with the tension force applied to the connector assembly, the therapy delivery element includes a percent elongation in a range between about 5% to about 30%.

7. The therapy delivery element of claim 1, wherein, with the tension force applied to the free floating end of the braided structure, the therapy delivery element includes a yield strength in a range between about 8 lbs. to about 15 lbs.

8. The therapy delivery element of claim 1, wherein, with the tension force applied to the connector assembly, the therapy delivery element includes a yield strength in a range between about 1 lb. to about 7 lbs.

9. The therapy delivery element of claim 1, wherein an axial force required to fully stretch the therapy delivery element between the connector assembly and the distal end of the outer tubing is less than about 10% of the yield strength between the free floating proximal end of the braided structure and the electrode assembly.

10. The therapy delivery element of claim 1, wherein a yield strength of the therapy delivery element when the tension force is applied to the free floating proximal end of the braided structure is at least 5 times greater than the yield strength when the tension force is applied to the connector assembly.

11. The therapy delivery element of claim 1, wherein the braided structure extends substantially to a distal end of the electrode assembly.

12. The therapy delivery element of claim 1, comprising an inner tubing bonded to the braided structure, the outer tubing surrounding the inner tubing.

13. The therapy delivery element of claim 12, wherein the inner tubing extends substantially to a distal end of the electrode assembly.

14. The therapy delivery element of claim 1, comprising at least one fixation structure attached to the therapy delivery element near the electrode assembly.

15. The therapy delivery element of claim 1, comprising a thermoplastic material melted into engagement with the braided structure.

16. A therapy delivery element configured for at least partial insertion in a living body, the therapy delivery element comprising:
a conductor assembly including a conductor;
an electrode assembly located at a distal end of the conductor assembly, the electrode assembly including an electrode electrically coupled to the conductor;
a connector assembly located at a proximal end of the conductor assembly, the connector assembly including an electrical contact electrically coupled to the conductor;
a plurality of fibers forming a braided structure surrounding the conductor assembly along a braided section, the braided structure including a distal end attached to the electrode assembly and a free floating proximal end located proximate the connector assembly; and
an outer tubing surrounding the braided structure along an outer tubing section, the outer tubing including a proximal end attached to the connector assembly and a distal end attached to the braided structure proximate the electrode assembly or to the electrode assembly, wherein the free floating proximal end of the braided structure is unattached to, but disposed within the outer tubing, and wherein:
with a proximal tension force applied to the connector assembly, an elongation of the therapy delivery element substantially corresponds to an elongation of the outer tubing and the conductor assembly;
with the proximal tension force applied to the free floating proximal end, the elongation of the therapy delivery element substantially corresponds to an elongation of the braided structure; and
the elongation of the therapy delivery element with the proximal tension force applied to the connector assembly is greater than the elongation of the therapy delivery element with the proximal tension force applied to the free floating proximal end.

17. The therapy delivery element of claim 16, wherein the braided structure includes a lumen, the conductor assembly being at least partially disposed within the lumen.

18. The therapy delivery element of claim 16, wherein the braided structure is bonded to the electrode assembly.

19. The therapy delivery element of claim 16, comprising an inner tubing bonded to the braided structure, the outer tubing surrounding the inner tubing.

20. The therapy delivery element of claim 19, wherein an inner diameter of the outer tubing is greater than an outer diameter of the inner tubing to form a gap between the inner tubing and the outer tubing.

21. A therapy delivery element configured for at least partial insertion in a living body, the therapy delivery element comprising:
a conductor assembly comprising a plurality of conductors;
an electrode assembly located at a distal end of the conductor assembly, the electrode assembly comprising a plurality of electrodes that are electrically coupled to the conductors;
a connector assembly located at a proximal end of the conductor assembly, the connector assembly comprising a plurality of electrical contacts that are electrically coupled to the conductors;
a plurality of fibers comprising a braided structure surrounding the conductor assembly along a braided section, the braided structure comprising a distal end attached to the electrode assembly and a free floating proximal end located near the connector assembly; and
an outer tubing surrounding the braided structure along an outer tubing section, the outer tubing comprising a proximal end attached to the connector assembly and a distal end attached to the braided structure near the electrode assembly or to the electrode assembly, wherein the free floating proximal end of the braided structure is unattached to, but disposed within, the outer tubing, and wherein:
with a proximal tension force applied to the connector assembly, an elongation of the therapy delivery element substantially corresponds to an elongation of the outer tubing and the conductor assembly;
with the proximal tension force applied to the free floating proximal end, the elongation of the therapy delivery element substantially corresponds to an elongation of the braided structure; and
an axial force required to fully stretch the therapy delivery element between the connector assembly and the distal end of the outer tubing is less than about 10% of the yield strength between the free floating proximal end of the braided structure and the electrode assembly.

22. A therapy delivery element configured for at least partial insertion in a living body, the therapy delivery element comprising:
a conductor assembly comprising a plurality of conductors;
an electrode assembly located at a distal end of the conductor assembly, the electrode assembly comprising a plurality of electrodes that are electrically coupled to the conductors;
a connector assembly located at a proximal end of the conductor assembly, the connector assembly comprising a plurality of electrical contacts that are electrically coupled to the conductors;

a plurality of fibers comprising a braided structure surrounding the conductor assembly along a braided section, the braided structure comprising a distal end attached to the electrode assembly and a free floating proximal end located near the connector assembly; and an outer tubing surrounding the braided structure along an outer tubing section, the outer tubing comprising a proximal end attached to the connector assembly and a distal end attached to the braided structure near the electrode assembly or to the electrode assembly, wherein the free floating proximal end of the braided structure is unattached to, but disposed within, the outer tubing, and wherein:

with a proximal tension force applied to the connector assembly, an elongation of the therapy delivery element substantially corresponds to an elongation of the outer tubing and the conductor assembly;

with the proximal tension force applied to the free floating proximal end, the elongation of the therapy delivery element substantially corresponds to an elongation of the braided structure; and a yield strength of the therapy delivery element when the proximal tension force is applied to the free floating proximal end of the braided structure is at least 5 times greater than the yield strength when the proximal tension force is applied to the connector assembly.

* * * * *